(12) United States Patent
Sanpitak (10) Patent No.: US 7,692,800 B2
(45) Date of Patent: Apr. 6, 2010

(54) MULTI-LEVEL LIGHT CURTAIN WITH STRUCTURE LIGHT SOURCES AND IMAGING SENSORS

(75) Inventor: Patanit Sanpitak, Highland Park, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 363 days.

(21) Appl. No.: 11/833,634

(22) Filed: Aug. 3, 2007

(65) Prior Publication Data

US 2009/0033940 A1    Feb. 5, 2009

(51) Int. Cl.
*G01B 11/14* (2006.01)
(52) U.S. Cl. .................................. 356/614; 356/615
(58) Field of Classification Search ............... 356/614
See application file for complete search history.

(56) References Cited

U.S. PATENT DOCUMENTS

| | | | |
|---|---|---|---|
| 4,995,716 A * | 2/1991 | Warnicki et al. | 351/212 |
| 5,159,361 A * | 10/1992 | Cambier et al. | 351/212 |
| 5,541,403 A | 7/1996 | Heinonen et al. | |
| 6,909,799 B1 * | 6/2005 | Wildmann et al. | 382/152 |
| 6,949,747 B2 | 9/2005 | Stark et al. | |
| 6,970,254 B2 * | 11/2005 | Hall | 356/614 |
| 7,328,871 B2 * | 2/2008 | Mace et al. | 246/169 R |
| 7,421,112 B2 * | 9/2008 | Calver et al. | 382/154 |
| 7,577,285 B2 * | 8/2009 | Schwarz et al. | 382/141 |
| 2004/0046967 A1 * | 3/2004 | Hall | 356/614 |
| 2006/0017911 A1 * | 1/2006 | Villar et al. | 356/4.01 |
| 2006/0231685 A1 * | 10/2006 | Mace et al. | 246/169 R |
| 2007/0280501 A1 * | 12/2007 | Walton | 382/100 |
| 2008/0170238 A1 * | 7/2008 | Ochi et al. | 356/610 |

OTHER PUBLICATIONS

Office Action for corresponding U.S. Appl. No. 11/833,618, dated Aug. 12, 2009, pp. 1-7, US.

* cited by examiner

*Primary Examiner*—Roy Punnoose
(74) *Attorney, Agent, or Firm*—Peter Kendall (57) ABSTRACT

Systems and methods for detecting an obstruction in a detector surface fields are provided. In one respect, a set of lines may be projected over substantially a half of the detection area and may subsequently imaged and evaluated. Other embodiments may include a second set of lines that may be projected over substantially a second half of the detection area and may subsequently imaged and evaluated. The images may be evaluated to determine if there are breaks (e.g., an obstruction) in the projected set of lines. Based on the evaluation, the detector may provide dynamic feedback signals to a processor, which may adjust the position of the detector or provide a signal indicating an obstruction.

20 Claims, 8 Drawing Sheets

MULTI-LEVEL LIGHT CURTAIN WITH STRUCTURE LIGHT SOURCES AND IMAGING SENSORS

CROSS-REFERENCE TO RELATED APPLICATIONS

This application incorporates by reference in its entirety to U.S. patent application Ser. No. 11/833,618, entitled "Optical Patient Detection System for Non-Circular Orbits," by Bak et al., filed on Aug. 3, 2007.

TECHNICAL FIELD

The invention relates to an imaging process, and in particular, feedback systems and methods for detecting an obstruction in a detection surface area.

BACKGROUND

Nuclear medical imaging is widely used due to the ease of collecting multiple data sets simultaneously during an imaging period. Emissions of a distributed radioactive tracer inside an organism are collected by detectors, converted into signals, and used to generate a complete image of the organism.

Generally, in single photon emission computerize tomography (SPECT), also referred to as a gamma camera system, scintillation detectors are placed relatively close to a patient during the image acquisition process. In some respects, light rails may be placed along each side of a scintillation detector surface to provide feedback signals to a motion control system that can automatically position the scintillation detectors at the closest proximity between the detector's surface and an object being imaged, such as a patient. The placement is important as the closer the detector is to the patient, the better the image quality. Also, maintaining a patient's safety is important with respect to the detector's placement. The detectors can each weigh upwards of 1000 pounds. Therefore, the placement of the detector in proximity of the patient is such that any contact with the patient may trigger a touch sensor and shut down the motion of the detectors.

Figure 1:
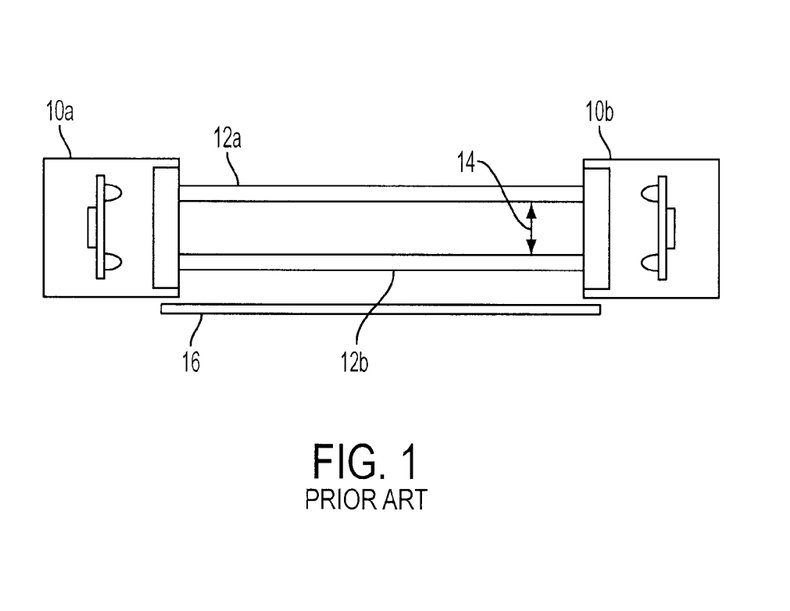
FIG. 1 shows a profile view of light rails in a conventional implementation.
Figure 2:
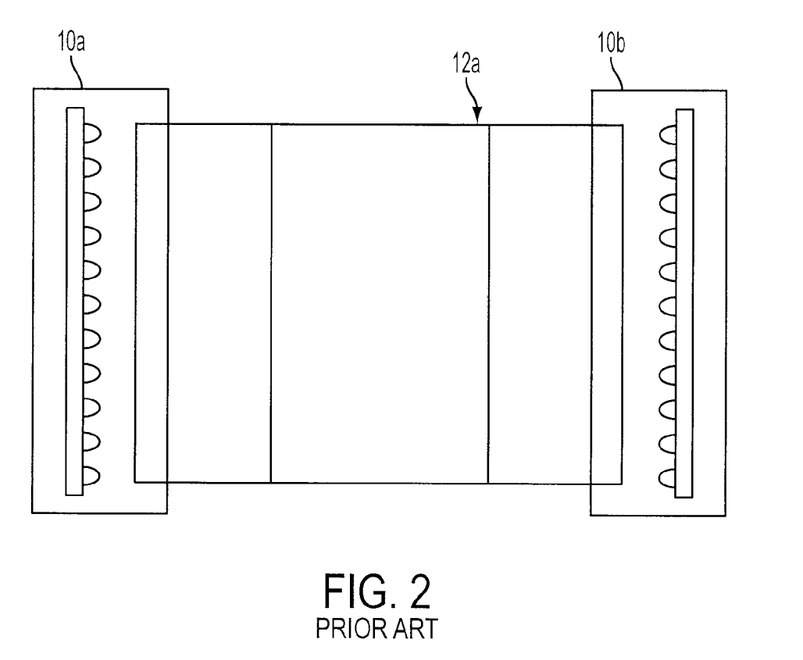
FIG. 2 shows a top view of the light rails of FIG. 1.

Current SPECT systems employ a two level light rail system that includes arrays of infrared light emitting diodes (IR LEDs), as shown in FIGS. 1 and 2, which illustrate a profile view and a top view of existing light rails 12a and 12b, respectively. Because each IR LED transmits its beam in a wedge shape across the surface of detector collimator 16, several IR LEDs may be arranged on both sides of the light rails in light transmitter and receiver 10a and 10b such that all wedge beams can interleave and generate a continuous plane over the surface of detector collimator 16. Generally, the IR LEDS and IR photodiodes may be sequentially scanned by a microcontroller for real-time sensing response as well as well as to prevent cross-talk between each light plane.

However, component parametric variations including sensitivity of the photodiodes and light intensity of the IR LEDs require component sorting and complex calibration scheme in order to function properly. Additionally, tight tolerance is required to assemble the IR LEDs and IR photodiodes on long printed circuit boards (PCBs) to meet the specified light plane sensitivity. Further, the PCBs are difficult to manufacture and handle.

Aside from the hardware limitations of current SPECT implementations, factors such as signal connection reliability may be compromised due to a large number of signal interfaces that are needed between the light rails and the microcontroller.

SUMMARY

In accordance with the teachings of the present disclosure, disadvantages and problems associated with existing light rails in imaging systems may be substantially reduced or eliminated. The present disclosure provides a multi-level light curtain using structured light sources and imaging sensors for detecting obstructions across a detection area, or an area.

In one respect, a system is provided. The system may include a laser module, such as a dual line laser module. The laser module, housed in a first housing unit, may project a set of lines across a detection area. An image of the projected lines may be captured by an image sensor. The captured image may be evaluated to determine breaks in the projected lines.

The method may also provide a second set of laser module. The second set of laser modules may be housed in a second housing unit and may be placed diagonally opposite the laser modules in the first housing unit. The second set of laser modules may be configured to project a second set of lines across the detection area.

The system may also include a second image sensor. In one respect, the second image sensor may be housed in the second housing unit and may be positioned diagonally opposite the image sensor within the first housing unit. The second image sensor may be coupled to the second set of laser modules and may be configured to capture an image of the projected lines from the second set of modules.

A control processor coupled to the first and second image sensors may be configured to evaluate the images captured by the respective image sensors. In one respect, the processor may evaluate whether the lines captured in the images include a break in the line or is seamless. Depending on the evaluation of the control processor, the motion control unit may adjust a position of a detector, such as a scintillation detector of a gamma camera system.

In other respects, a method for detecting an obstruction in a detection area may be provided. The method may provide steps for projecting a first set of lines across substantially a first half of a detection area and projecting a second set of lines across substantially a second half of the detection area. For each of the projections, an image is captured and evaluated. In one embodiment, the images are evaluated to determine if the lines captured include breaks (e.g., an obstruction in the detection area) or are seamless. Based on the evaluation, a detector may be positioned relative to an object.

In some respects, a method for detecting an obstruction may provide steps for projecting a first line on a first plane and a second line on a second plane that may be spaced apart from the first plane. The projections may be across a testing surface, where the first line and second line may project over substantially a first half of a detection area. Similarly, the method may provide steps for projecting a third line on a third plane and forth line on a forth plane that may be spaced apart from the third plane across the testing surface area. The third line and forth line may project over a second half of the detection area. The method may provide for capturing a first image of the first and second lines projections and a second image of the third and forth line projections. The captured images may be evaluated to determine if the first line, second line, third line, and/or forth line include a break. Depending on the evaluation of the captured images, in the embodiment where a detection camera (collectively a detector) is placed relative to an object, e.g., patient, specimen, etc., the position of the detector may be changed.

It is understood that the methods of the present disclosure may include instructions that may be executed on a tangible computer media.

BRIEF DESCRIPTION OF THE DRAWINGS

The embodiments will be explained in greater detail in the text which follows by means of diagrammatically represented embodiments in the drawing without the invention being restricted to these embodiments.

DETAILED DESCRIPTION

Preferred embodiments and their advantages are best understood by reference to FIGS. 1 through 6c, wherein like numbers are used to indicate like and corresponding parts.

Figure 3A:
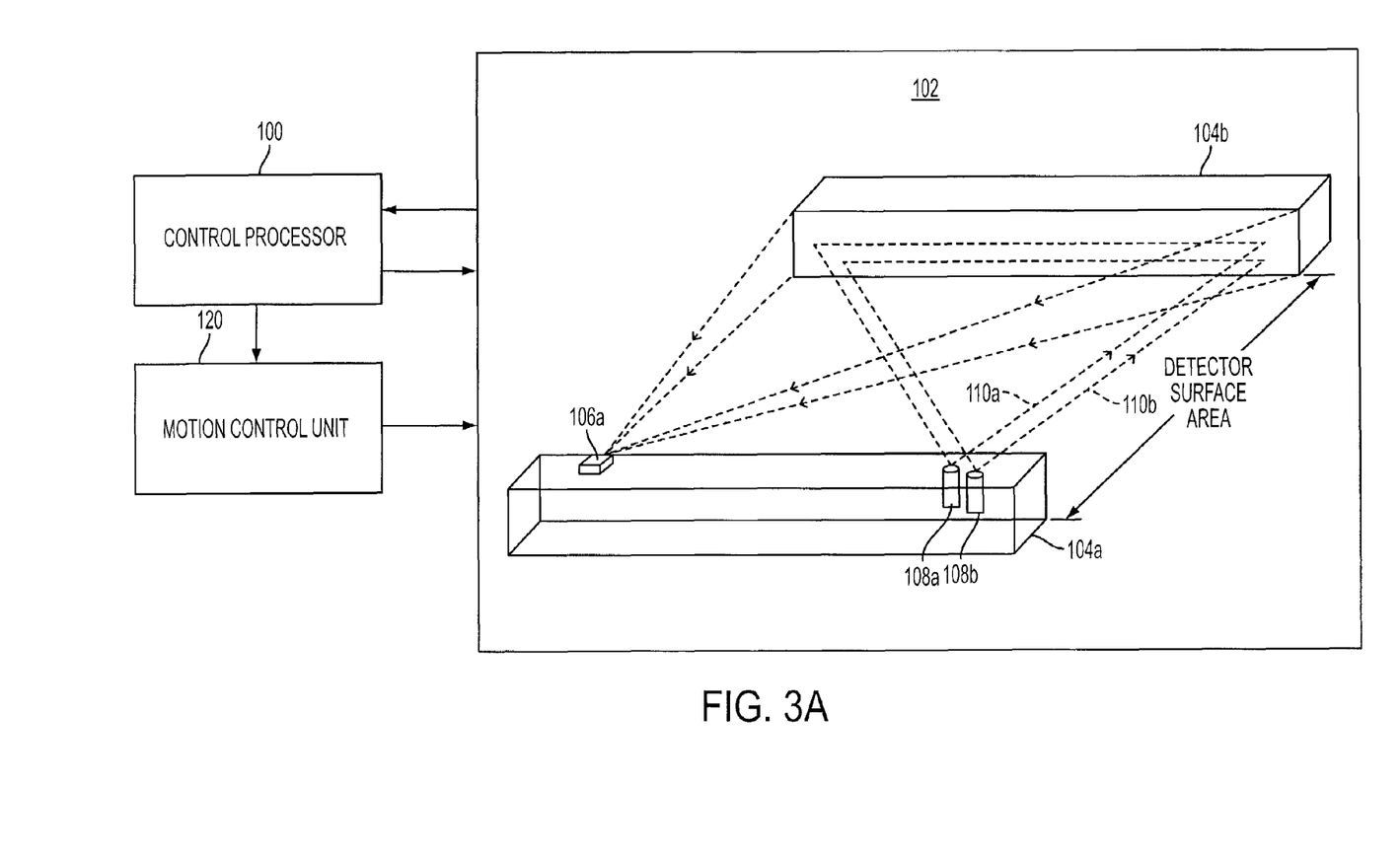
FIGS. 3A and 3B show a block diagram of a multi-level housing system, in accordance with embodiments of the present disclosure.

The present disclosure provides a replacement of existing light rails in detectors with a multi-level light curtain that may use multiple light sources and multiple imaging sensors. Referring to FIG. 3A, light curtain 102 coupled to control processor 100 is shown. Light curtain 102 may include housings 104a and 104b (collectively, housings 104). In at least one of the housings 104a or 104b, at least one image sensor and at least one laser module are stored. Although only one image sensor 106a and laser modules 108a and 108b are depicted in housing 104a of FIG. 1, it is understood that housing 104b may also include similar components. It is also understood that more than one image sensor and one or more laser modules may be provided in each of the housings 104.

Figure 3B:
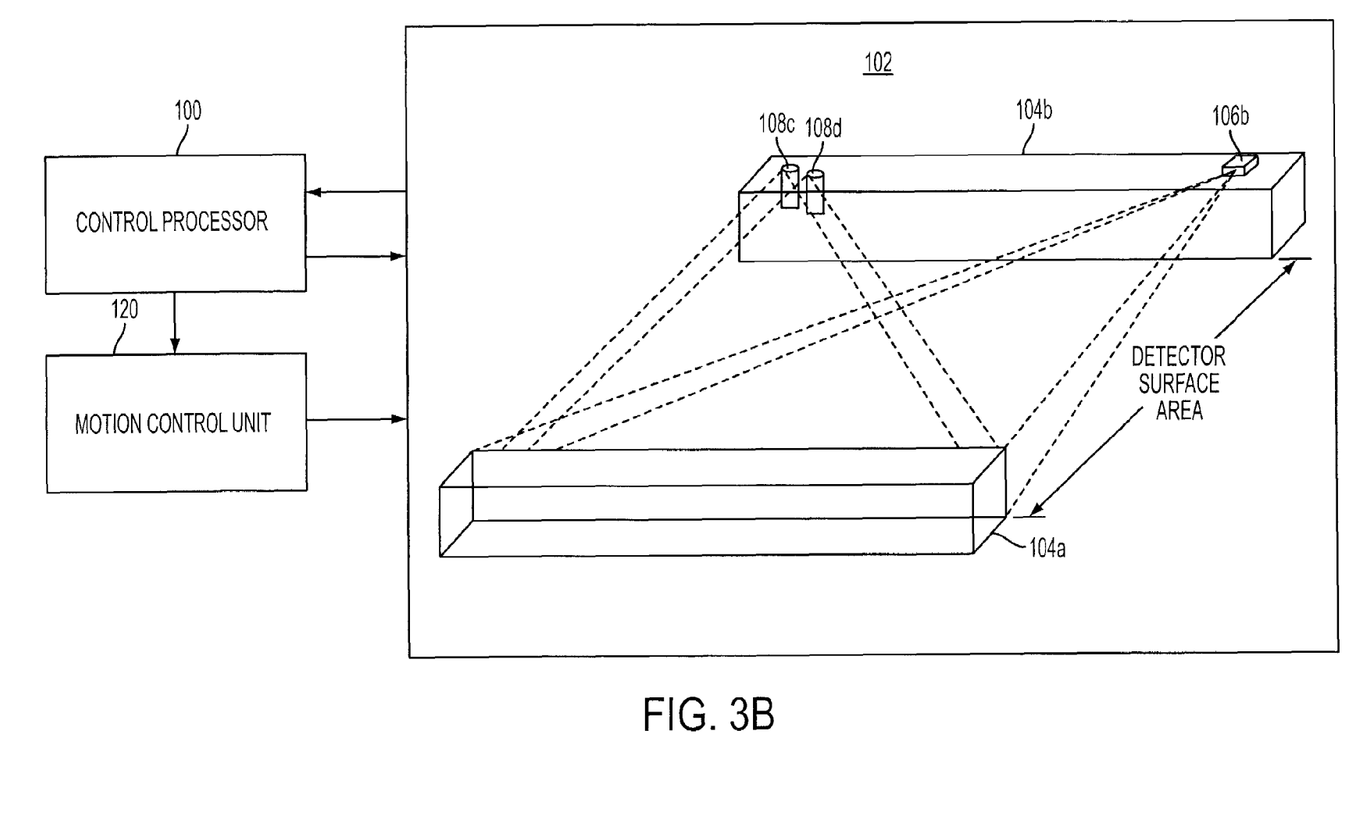

In one embodiment, each housing 104a and 104b include at least one laser module and at least one image sensor. Housing 104b may include at least one laser module 108c and 108d placed in an opposite corners of an image sensor within housing 104b, as shown in FIG. 3B. For a better overview the laser module and image sensor in housing 104a are not shown in FIG. 3B. In some respects, a laser module of housing 104b may be placed diagonally opposite of laser modules 108a and 108b of housing 104a. Similarly, image sensor 106b in housing 104b may be placed diagonally opposite of image sensor 106a of housing 104a. Other configurations, including placement of image sensors and laser modules directly or indirectly across from one another in the respective housing are contemplated.

To project lines across the detection area, a two line laser module, such as 2X Apinex Module LN-60 line lasers may be used, as shown in FIGS. 3A and 3B. The modules may be vertically separated to generate 2 lines that project on two different planes. For example, laser modules 108a and 108b may be vertically offset in housing 104a such that the projections may be approximately one (1) centimetre apart. It is understood that the distance between the projections may vary in distance (e.g., may be greater than or less than one centimetre) depending on the application.

Each line laser module may generate a fan beam which covers about half of the detection area. For example, line laser module 108a may provide first projected line 110a and line laser module 108b may provide second projected line 110b, where the projected lines each cover approximately half of the detection area, as shown in FIG. 3A. An obstruction occurring outside of the projected line planes may not be detected or may interfere with the capturing of the image by an imaging sensor. Therefore, in some embodiments, by providing a similar configuration in housing 104b, e.g., two line laser modules, the projection may cover a second half of the detection area, as shown in FIG. 3B.

In a multiple light plane configuration, multiple line laser modules may be used. For example, referring to FIGS. 3A and 3B, for dual light planes, a total of four line laser modules may be needed (e.g., two line lasers in each housing). A beam splitter optic (not shown) coupled to the modules may be used to generate two lines from a single laser module.

In a SPECT system, scintillation detectors are placed as close as possible in relation to a patient or specimen without the patient or specimen interfering with or blocking the detection surface area. More particularly, the placement of the detectors may be such that the detectors may obtain the best quality image, while maintaining the safety of the patient or specimen (e.g., the detectors does not touch the patient or specimen). In order to determine the placement and adjustment of the detectors, the system shown in FIGS. 3A and 3B and the techniques described in FIGS. 4 through 6 may provide a dynamic feedback to a motion control unit (e.g., motion control unit 120 coupled to light curtain 102) to adjust the position of the scintillation detectors. In particular, when an object obstructs the light plane, the projected line or lines may be broken which can be detected by an image processing unit and each light plane status signal may be sent to the motion control processing system.

Figure 4:
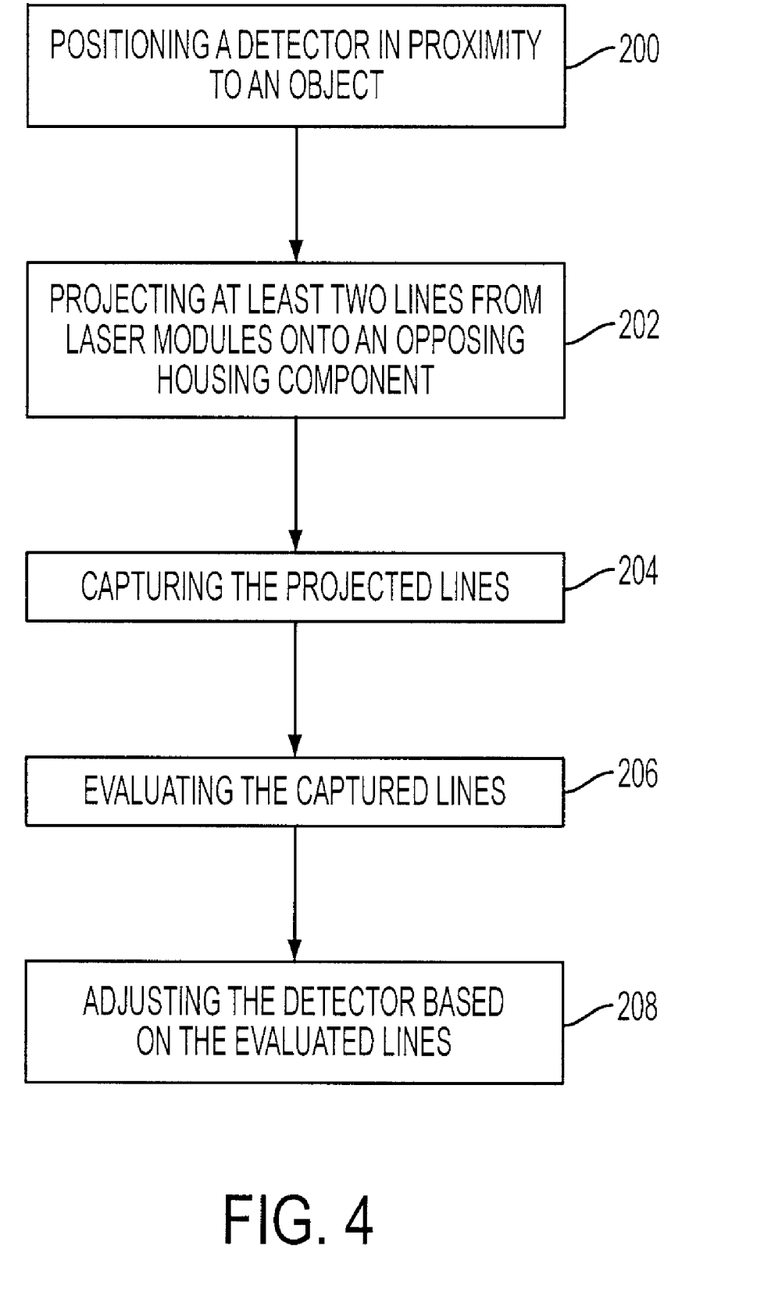
FIG. 4 shows a flowchart of a method, in accordance with embodiments of the present disclosure.

First the detectors may be positioned using a motion controller (e.g., motion control unit 120) in proximity to the object (step 200). The detectors may be aligned before and/or after the object is situated.

In step 202 of FIG. 4, lines from laser modules may be projected onto an opposing housing component, similar to projected lines 110a and 110b onto housing 104b from line laser modules 108 of FIG. 3A. The projections of the lines aimed towards a housing component may be at an angle such that two (2) lines along the length of the housing appear. It is understood that more than two line projections may be projected and evaluated.

In one respect, the projection of the lines may include only a projection from one housing component onto an opposing housing component (also referred to as a test surface). Alternatively, the projection may include a projection from multiple laser modules, and in particular, at least two line projections from each housing component of a light curtain (e.g., projections from housing 104b onto housing 104a and projections from housing 104a onto housing 104b of FIGS. 3A and 3B).

In step 204, the projected lines from the laser modules may be captured. Imaging sensors such as, but not limited to, CMOS imaging sensors (e.g., Phillips PC camera model SPC600NC) may be used to capture the multiple projected lines. For example, imaging sensor 106a or 106b may be aimed at an appropriate angle to capture the entire length of the test surface, or housing 104b. The captured projected lines from imaging sensor 106a and/or 106b may be processed by control processor 100.

Next, the captured lines from step 204 may be evaluated in step 206 followed by an adjustment of the detector's position in step 208. In one embodiment, a control processor (e.g., control processor 106) may evaluate the captured projected lines to determine if the projected lines are broken, i.e., an object is obstructing the line projections from the laser modules. The position of the detector relative to the object may depend on whether one or all of the projected lines are obstructed. For example, in an embodiment where two lines are projected, both lines may be evaluated. If both lines are broken, the object may be too close to the detector and may interfere with the imaging process or is located too close to the object and may hinder the object's safety. If both lines are not broken, the detector may not be close enough to an object and may need to be repositioned. If only one line is broken, the detector's position may be situated as close as possible to the object.

Figure 5:
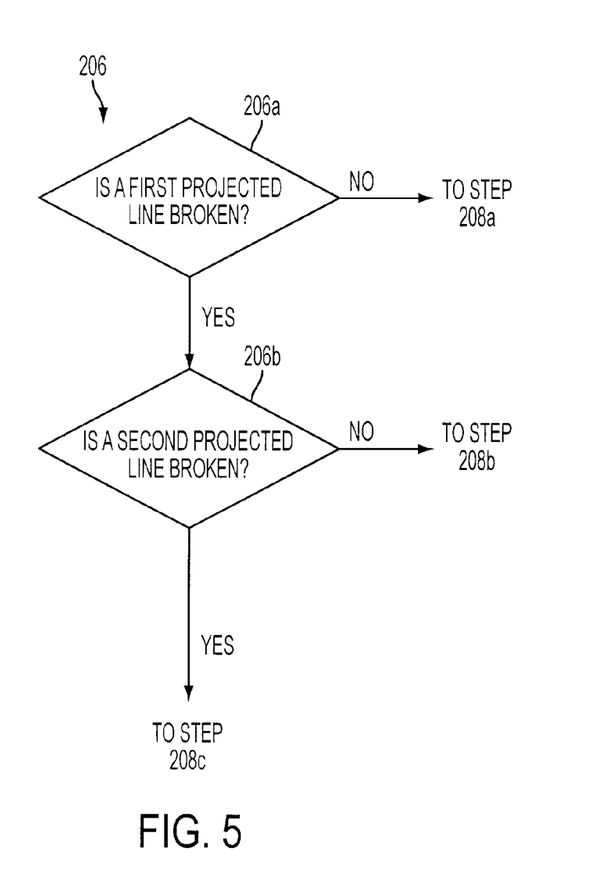
FIG. 5 shows steps for evaluating captured projected lines, in accordance with embodiments of the present disclosure.

Referring to FIG. 5, steps 206 is shown in more detail where two lines are projected. In one respect, a first line closest to the object may first be evaluated. For example, referring to FIG. 3, project line 110b is projected on a plane below line 110a and hence, is closest to the object and may first be evaluated by control processor 100. In one embodiment, if the first line is not broken, the detector may be moved closer to the object as shown in step 208a of FIG. 6A. Steps 202, 204, and 206 may subsequently be performed to evaluate the position of the detector relative to the object.

If the first line is broken, an object may be obstructing a portion of the detection area. However, at that position, the detector may be suitable for some applications. As such, to determine if the object is too close to the detector, the second line projected (e.g., line 110a of FIG. 3) by the line laser modules may be evaluated as shown in step 204b of FIG. 5. If the second line projection is not broken, then the detector's position may be located as close to the object as possible without obstructing the entire detection area. Thus, in step 208b the detector may maintain its position and subsequent imaging techniques known in the art may commence.

If the second line evaluated is also broken, this may indicate that the detector may be too close to the object. Therefore, in step 208, and in particular, step 208c of FIG. 6c, the detector may be moved away from the object. Steps 202, 204, and 206 may be subsequently may be performed to determine if the new position is appropriate for imaging.

In one embodiment, step 206 may involve an algorithm readable on a computer readable media, such as a test application software written in, for example, Visual Basic 6.0 running on a Windows PC environment or other suitable application running on a different or similar platform, for evaluating the captured line projections. The control processor may communicate with the imaging sensor via an interface such as a USB port or other network ports known in the art.

Figure 7:
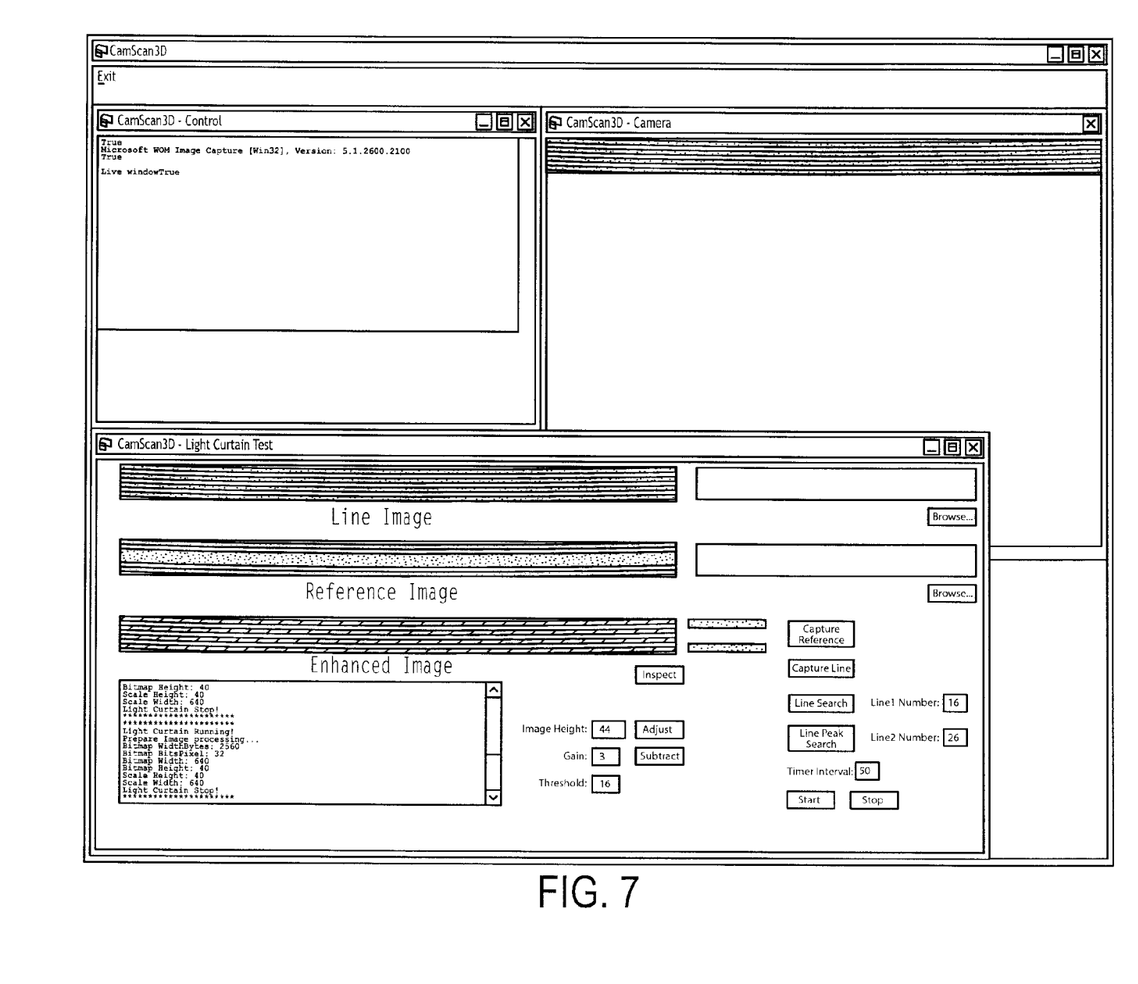
FIG. 7 shows a line enhanced image, in accordance with embodiments of the present disclosure.

In order to evaluate the lines captured by the imaging sensor in step 204, the algorithm may include instructions for performing a setup/calibration test prior to the placement of the detector relative to an object. In particular, a reference image of a test surface without any line projections may be captured by the imaging sensor. Next, an image of lines projected by the line modules may be captured. The reference image may be subtracted from the image of the lines projection which may result in a line enhanced image, as shown in FIG. 7. Next, a line peak search to locate the X, Y coordinate peak positions of the lines projected may be determined and stored for reference.

In step 206 of FIG. 5, the captured image may be subtracted from the line enhanced image from the setup/calibration test resulting in a test image. To determine if there are breaks in the captured lines, the test image may be compared with the line peak coordinates.

Figure 6A:
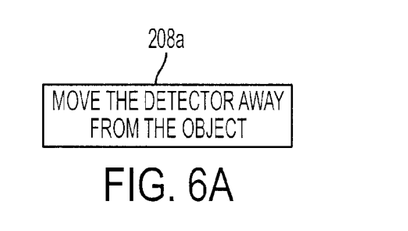
FIGS. 6a, 6b, and 6c each show steps for adjusting a detector as a result from the steps shown in FIG. 5, in accordance with embodiments of the present disclosure.
Figure 6B:
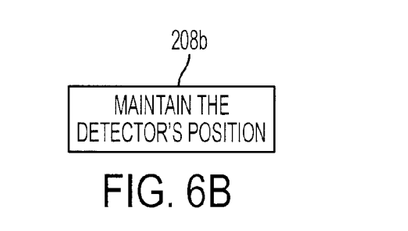
Figure 6C:
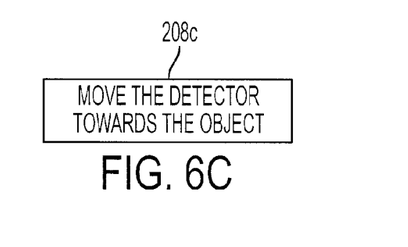
Figure 8:
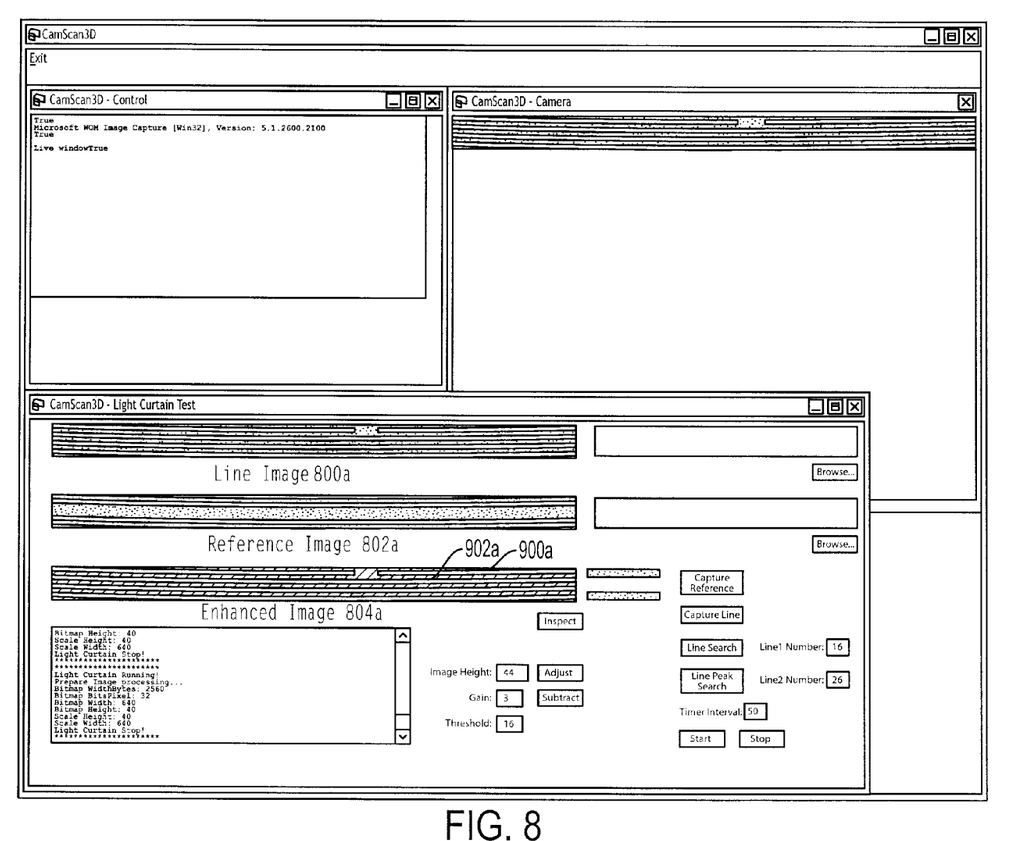
FIG. 8 shows an output of an evaluation step, in accordance with embodiments of the present disclosure.
Figure 9:
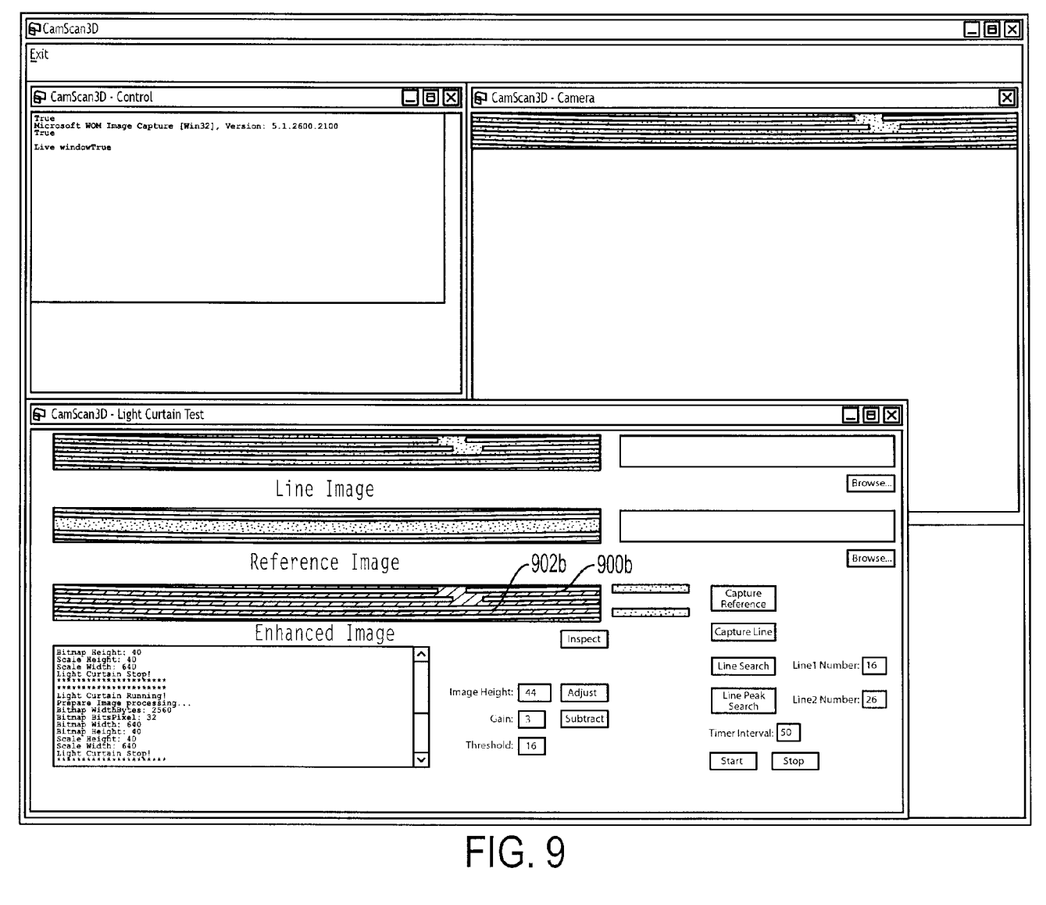
FIG. 9 shows an output of an evaluation step, in accordance with embodiments of the present disclosure.

Depending on the results of the comparison, the detector may be moved as shown in FIGS. 6a, 6b, and 6c. Referring to FIGS. 8 and 9, results of an evaluation step is shown. In FIG. 8, line image 800a may be captured from a projection across a detection surface. Reference image 802 may be subtracted from line image 800a resulting in enhanced image 804a. As seen from FIG. 8, first line 900a is blocked by an object and second line 902a is seamless. Similarly, as seen in FIG. 9, after the processing of line image 800b and reference image 802b, enhanced image 804b shows that both first line 900b and second line 902b are blocked by an object during the scanning phase, respectively. These images may be displayed to a user or technician for manual adjustment of the detector's position. Alternatively, the results of the comparison may be provided to a motion control unit coupled to the control processor for dynamic adjustment of the detector's position.

In other respects, step 206 and 208 may be implemented with a low cost DSP (Digital Signal Processor) or FPGA (Field Programmable Gate Array) logic. One of ordinary skill in the art can recognize these and other algorithms or hardware system may be used to evaluate the captured line images and reposition the detector when necessary.

Light curtain 102 of FIG. 3 and the some or all of the steps shown in FIG. 4 may also be used for other applications. In one embodiment, the curtain may be applied for safety and alarm type systems. For example, the light curtain may be used as a barrier. Steps 202 through 206 of FIG. 4 may be implemented. Instead of a motion control unit, the system may include an output means for indicating that there is an obstruction in the detector area. As such, in a subsequent step, an output either visually or audibly provided to a user may provided indicating an object that blocks one or more of the projected lines. It is understood that the light curtain of the present disclosure may be used in any application where detecting an object over an area is needed. One of ordinary skill in the art can recognize that elements of the system shown in FIG. 3 may be modified to adapt to various detector size areas.

As used in this disclosure, "tangible computer readable media" means any instrumentality, or aggregation of instrumentalities that may retain data and/or instructions for a period of time. Tangible computer readable media may include, without limitation, random access memory (RAM), read-only memory (ROM), electrically erasable programmable read-only memory (EEPROM), a PCMCIA card, flash memory, direct access storage (e.g., a hard disk drive or floppy disk), sequential access storage (e.g., a tape disk drive), compact disk, CD-ROM, DVD, and/or any suitable selection of volatile and/or non-volatile memory and/or storage.

The computer-readable media may be embodied internally or externally on a hard drive, ASIC, CD drive, DVD drive, tape drive, floppy drive, network drive, flash drive, USB drive or the like. Further, the computer-readable media may be any computing device capable of executing instructions for implementing the method shown, for example, in FIGS. 4, 5, and 6a-c. In one embodiment, the computer-readable media may be a personal computer (e.g., a typical desktop or laptop computer operated by a user). In other embodiments, a computer-readable media may be a personal digital assistant (PDA) or other handheld computing device.

In some embodiments, the computer-readable media may be a networked device and may constitute a terminal device running software from a remote server, wired or wirelessly. Input from a user or system components may be gathered through one or more known techniques such as a keyboard and/or mouse. Output, if necessary, may be achieved through one or more known techniques such as an output file, printer, facsimile, e-mail, web-posting, or the like. Storage may be achieved internally and/or externally and may include, for example, a hard drive, CD drive, DVD drive, tape drive, floppy drive, network drive, flash, or the like. The computer readable-media may use any type of monitor or screen known in the art, for displaying information, such as the lines shown in FIGS. 7, 8, and 9. For example, a cathode ray tube (CRT) or liquid crystal display (LCD) can be used. One or more display panels may also constitute a display. In other embodiments, a traditional display may not be required, and computer readable-media may operate through appropriate voice and/or key commands.

What is claimed is:

1. A system comprising:
 a first laser module for projecting lines across a detector surface area, the laser module being housed in a housing unit;
 a first image sensor, the image sensor configured to capture an image of projected lines from the laser module;
 a control processor coupled to the image sensor, the control processor configured to calibrate a test image and evaluate the captured image based on the test image: and
 a motion control unit coupled to the control processor, the motion control unit configured to adjust position of a detector with respect to an object in response to determination by the control processor of whether the captured image is obstructed.

2. The system of claim 1 further comprising a second laser module, the second laser module projecting lines across the detector surface area, and wherein the second laser module is housed in a second housing unit opposite the first laser module, and
 a second image sensor for capturing an image of projected lines from the second laser module.

3. The system of claim 2 wherein the second laser module is arranged diagonally opposite the first laser module.

4. The system of claim 1, wherein the first laser module comprises two line laser modules.

5. The system of claim 4, wherein the two line Laser modules are set apart vertically to project two lines spaced apart.

6. The system of claim 1, wherein the image sensor comprising a CMOS image sensor.

7. A method for detecting an obstruction in a detector surface area, the method comprising:
 calibrating a test image of the detector surface area;
 projecting a first set of lines across substantially a first half of the detector surface area;
 projecting a second set of lines across substantially a second half of the detector surface area;
 capturing images of the projected first and second set of lines;
 evaluating the captured images with respect to the test image; and
 based on the evaluation, positioning a detector relative to an object.

8. The method of claim 7, wherein the step of capturing the images comprises capturing images of substantially the entire detection area.

9. The method of claim 7, wherein the step of evaluating comprises comparing the captured images of each of the projected first set of lines and projected second set of lines with a reference image.

10. The method of claim 9, wherein the step of comparing comprises determining peak positions of the lines in each captured image.

11. The method of claim 7, wherein the first set of lines is projected on a first plane and the second set of lines is projected on a second plane.

12. The method of claim 11, wherein the first line on the first plane is evaluated prior to evaluating the second line on the second plane.

13. The method of claim 12, further comprising maintaining the position of the detector relative to the object if the step of evaluating determines that the first projected line is obstructed.

14. The method of claim 12, further comprising positioning the detector in a direction away from the object if the step of evaluating determines that both the first and second projected lines are obstructed.

15. The method of claim 12, further comprising positioning the the detector in a direction closer to the object if the step of evaluating determines that both the first and second projected lines are not obstructed.

16. A method for detecting an obstruction in a detector surface area, the method comprising:
 calibrating a test image of the detection surface area:
 positioning a detector relative to an object;
 projecting a first line on a first plane and a second line on a second plane across a testing surface, the first line and second line projecting over substantially a first half of the detection surface area;
 projecting a third line on a third plane and fourth line on a fourth plane across the testing surface area, the third line and fourth line projecting over a second half of the detection surface area;
 capturing a first image of the first and second line;
 capturing a second image of the third and fourth line;
 evaluating the first and second images with respect to the test image; and
 repositioning the detector relative to the object based on the evaluation of the first and second images.

17. The method of claim 16, wherein the first and second lines are projected from a first dual laser line module housed in a first housing unit.

18. The method of claim 17, wherein the third and fourth lines are projected from a second dual laser line module housed in a second housing unit, the second dual laser line module being diagonally opposite of the first dual laser line module.

19. The method of claim 16, wherein capturing a first image comprises capturing an image with a first CMOS image sensor.

20. The method of claim 19, where capturing the second image comprises capturing an image with a second CMOS image sensor placed diagonally opposite of the first CMOS image sensor.

* * * * *